US00PP31693P2

(12) United States Plant Patent
Hansen

(10) Patent No.: US PP31,693 P2
(45) Date of Patent: Apr. 21, 2020

(54) ***ACHILLEA* PLANT NAMED 'SASSY SUMMER LEMON'**

(50) Latin Name: ***Achillea* hybrid**
Varietal Denomination: Sassy Summer Lemon

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,800

(22) Filed: Jan. 14, 2019

(51) Int. Cl.
*A01H 5/02* (2018.01)
*A01H 6/14* (2018.01)

(52) U.S. Cl.
USPC ..... Plt./263.1

(58) Field of Classification Search
USPC ..... Plt./263.1

CPC ..... A01H 5/02; A01H 5/025; A01H 5/0205; A01H 6/14; A01H 6/04
See application file for complete search history.

(56) References Cited

PUBLICATIONS

Germania Seed 2018 Walters Gardens Bare Root and Plug Perennials, retrieved on Sep. 23, 2019, retrieved from the Internet at https://www.germaniaseed.com/pdf/2019/749_walters.pdf, pp. 1,24. (Year: 2018).*
Walters Gardens, Inc. 2018 Summer Selections Price List & Order Forms, retrieved on Sep. 23, 2019, retrieved from the Internet at https://wgi-img.s3.amazonaws.com/cms/4838023d0a27c4d7d4ba5d7765922912.pdf, pp. 1-4. (Year: 2018).*

* cited by examiner

*Primary Examiner* — June Hwu

(57) ABSTRACT

The new and distinct Yarrow, *Achillea* plant named 'Sassy Summer Lemon', with narrow, silvery, fern-like foliage; tall, stiff, heavily branched peduncles with bright, sunny yellow inflorescences, beginning in mid-June and continuing for about six weeks. The new plant is useful for landscaping, as a specimen or en masse and as a cut flower.

1 Drawing Sheet

Botanical designation: *Achillea* hybrid.
Cultivar denomination: 'Sassy Summer Lemon'.

STATEMENT REGARDING PRIOR DISCLOSURES UNDER 37 CFR 1.77(B)(6)

The first public disclosure of the claimed plant, in the form of a sale, was made by Walters Gardens, Inc. on Jul. 9, 2018. Prior to that, on Feb. 1, 2018 the claimed plant was displayed as a photograph with a brief description on a website operated by Walters Gardens, Inc., who obtained the plant and all information relating thereto, from the inventor. No plants of *Achillea* 'Sassy Summer Lemon' have been sold, in this country or anywhere in the world, nor has any disclosure of the new plant been made, more than one year prior the filing date of this application, and such sale or disclosure within one year was either derived directly or indirectly from the inventor.

BACKGROUND OF THE PLANT

The present invention relates to the new and distinct yarrow herein also referred to as *Achillea* 'Sassy Summer Lemon', by the cultivar name, 'Sassy Summer Lemon', or as the new plant. The new plant was selected by the inventor as a single seedling resulting from an open pollination cross in an isolation block between 'Moonshine' (not patented) crossed with an unknown male parent on Jun. 23, 2014 in research facility of a wholesale perennial grower based in Zeeland, Mich., USA. The seeds from this cross were collected late summer of 2014. The single seedling was then isolated and compared in subsequent years to other Yarrow and subsequently found to be different from all cultivars known to the discoverer and eventually given the breeder code 14-53-1.

Asexual propagation beginning in the August of 2015 at the same nursery in Zeeland, Mich., USA by basal shoot cuttings has shown 'Sassy Summer Lemon' to be stable and reproduce true to type in successive generations.

SUMMARY OF THE PLANT

*Achillea* 'Sassy Summer Lemon' has not been observed in all possible environmental conditions. The phenotype may vary slightly with changes in environments such as light intensity, fertility, water availability, etc. without, however any variation in genotype.

*Achillea* 'Sassy Summer Lemon' is distinct from all cultivars known to the inventor in the following traits:

1. Narrow, silvery, fern-like foliage with medium height and dense upright habit.
2. Numerous large panicles of bright, sunny yellow inflorescences.
3. Heavily-branched peduncles with center main cluster to about 11 cm across.
4. Sturdy stems withstand wind and rain.
5. Flowering begins early-June and continues through mid-July.

Plants of *Achillea* 'Sassy Summer Lemon' are most similar to 'Moonshine' (not patented), 'Coronation Gold' (not patented), 'Sunny Seduction' U.S. Plant Pat. No. 20,808, 'Anblo' U.S. Plant Pat. No. 8,828, 'Sassy Summer Silver', copending U.S. Plant patent application Ser. No. 16/350,799 and 'Parker's Variety' (not patented). 'Moonshine' has deeper gold floret coloration, is slightly taller in habit, and the foliage shows susceptibility to *Botrytis*. 'Coronation Gold' has deeper yellow floret color and is significantly taller in habit. 'Sunny Seduction' has slightly deeper yellow floret color and is taller in habit in side by side trials. 'Anblo', sold under the tradename ANTHEA™ has paler yellow florets and is slightly taller than the new plant. 'Sassy Summer Silver' has a deeper gold floret color, flowering at least a week later, is taller in habit with more silvery foliage and less deeply cleft lobules. 'Parker Variety' is much taller and less compact in habit and the florets are deeper gold colored.

BRIEF DESCRIPTION OF THE DRAWINGS

The color drawings illustrate the overall characteristics of *Achillea* 'Sassy Summer Lemon' as a three-year-old plant grown in a full-sun trial garden in Zeeland, Mich. The colors are as true as reasonably possible given the technology available. The color values may vary slightly depending on light intensity and quality.

DETAILED BOTANICAL DESCRIPTION

Figure 1:
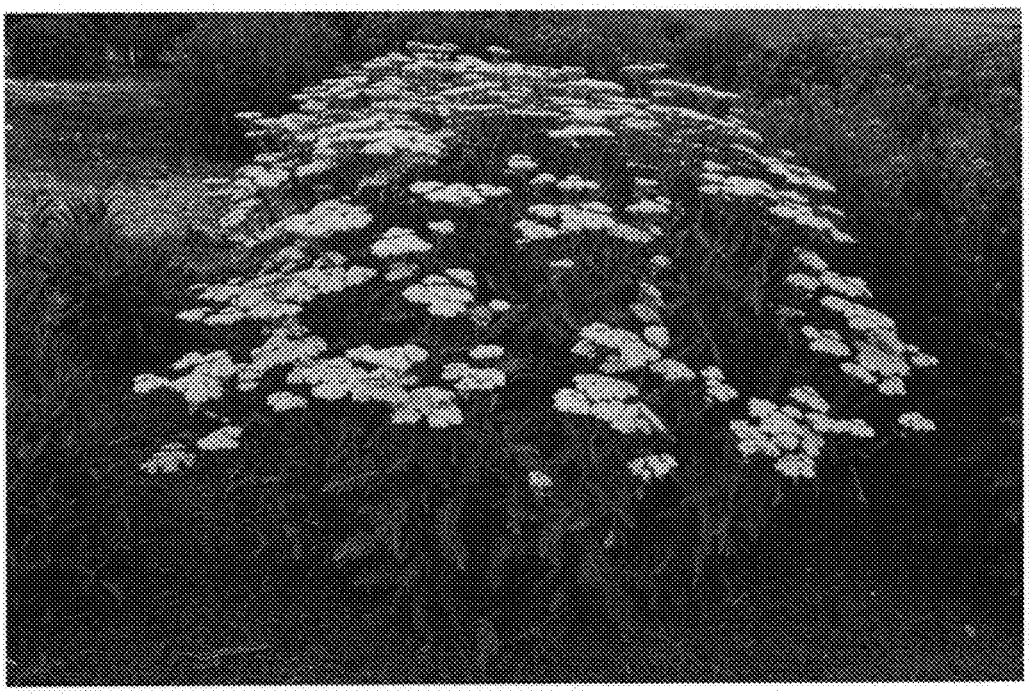
FIG. 1 shows the new plant in a trial facility.
Figure 2:
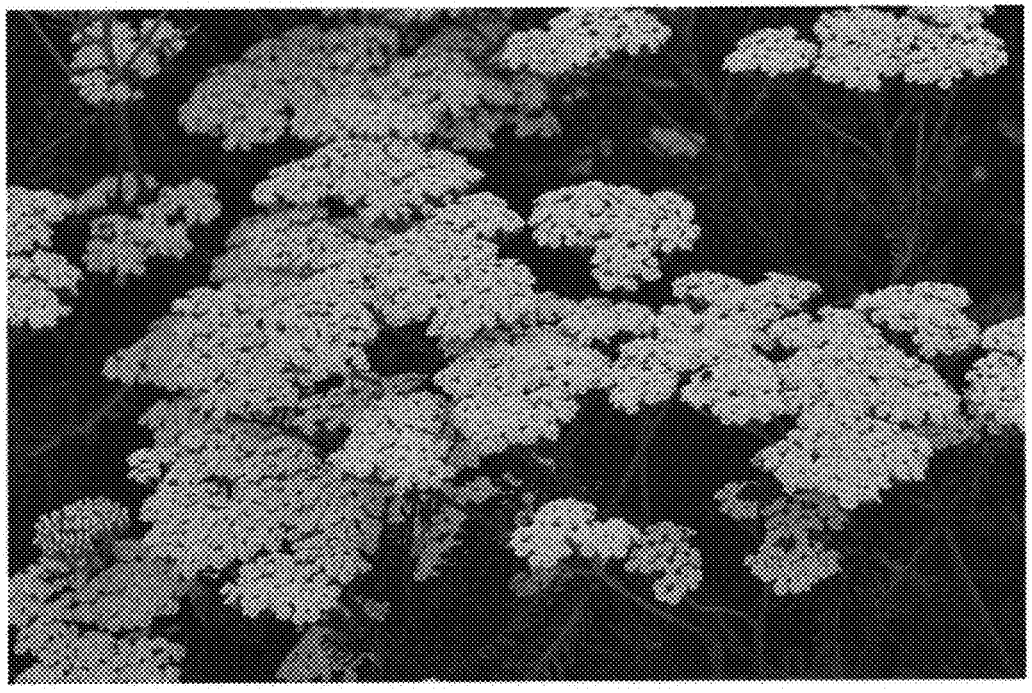
FIG. 2 shows a close-up of the flowers and buds of the new plant.

The following description is based on a three-year-old plant growing in a full-sun trial garden in Zeeland, Mich., USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: Female or seed parent is *Achillea* 'Moonshine'; the male or pollen parent unknown;

Asexual propagation: Basal shoot cuttings, about 10 to 14 days to initiate roots; time to finish as # 1 field grown size about 4 months from a 25 mm liner;

Plant habit: Dense axillary branches; upright, heavily-branched, herbaceous, winter-hardy, perennial mound; up to 35.0 cm tall and 95.0 cm wide; average about 33.0 cm tall and about 88.0 cm across;

Stems: Cylindrical; lanulose; branching near top; about 6.0 mm diameter and 30.0 cm long; up to 27 stems per plant, average 24 stems per plant;

Stem color: Nearest RHS 137A;

Internodes: About 16 per stem; same color as surrounding stem;

Leaves: Alternate; glabrous; pinnatisect with lobules deeply dissected; lanceolate; acute apex; base attenuate; sessile except most proximal cauline leaves; lanulose abaxial and adaxial; up to 31.0 cm long and 7.5 cm wide with individual lobes to 12.0 mm wide and 3.0 cm long, average about 14.0 cm long and 4.0 cm wide; fragrance lightly herbal;

Leaf color: Young expanding leaves adaxial nearest a blend of RHS 189B and RHS 139A and abaxial nearest a blend of nearest RHS 137A and RHS 188B; mature leaves adaxial nearest a blend of RHS 139A and RHS 188B, abaxial nearest a blend of RHS N138B and RHS 188C;

Veins: Pinnate; only abaxial midrib obvious;

Midrib color: Adaxial and abaxial nearest blend between RHS 150D and RHS 148D;

Inflorescence: Radiate; capitate; composite consisting of about five ray and about twenty disk florets; on heavily branched terminal stems; individual inflorescence about 8.0 mm diameter, about 8.0 mm tall from bottom of involucral bracts to top of exserted anthers; disk about 4.5 mm across; attitude mostly upright; producing branched stems with about 300 inflorescences per stem; average panicle about 11 cm across and 5 cm tall;

Receptacle: About 4.0 mm tall and 5.0 mm diameter; color nearest RHS 148C;

Inflorescence fragrance: Not detected;

Phyllaries: About ten in two whorls; lanceolate; acute apex; truncate base; margin entire; outer or lower set about 2.0 mm long and 1.0 mm across, inner set about 3.0 mm long and 1.0 mm across; glabrous adaxial, pubescent abaxial; tightly adpressed against ray petals;

Phyllary color: Nearest RHS 147C adaxial and abaxial, with margins nearest RHS 193C;

Flowering period: Mid-June, for about 6 weeks;

Flower longevity: 4 to 6 days;

Inflorescence buds: Ovoid; with ray florets still partially enclosed in phyllaries about 4.0 mm tall and 2.5 mm across;

Inflorescence bud color: Exposed ray florets nearest RHS 13A just above phyllaries; phyllaries color nearest RHS 146C;

Peduncle: Cylindrical; lanulose; strong; upright attitude; heavily branched; up to 6.0 mm diameter at base, average 5.0 mm diameter; and 35.0 cm long, flowering in upper 12.0 cm; branches to about 10.0 cm long and 4.0 mm diameter at base;

Peduncle color: Between RHS 146C and RHS 138B;

Ray florets: Imperfect; staminate; typically about five per inflorescence; containing only gynoecium with style about 2.5 mm long and split stigma;

Ray floret ligule: Blade with basal claw; blade apex tri-lobed, margin entire; base claw, attenuate; opening to form 90° angle; glabrous adaxial and adaxial; about 4.0 mm long and about 5.0 mm wide; basal claw about 1.5 mm long and about 0.5 mm across;

*Ray floret ligule color*.—Adaxial nearest RHS 9C, abaxial nearest RHS 2D and claw base nearest RHS NN155C with little to no change in color with maturity; at maturity adaxial between RHS 9C and RHS 9D, abaxial nearest RHS 2D.

*Style*.—Cylindrical; about 2.0 mm long and 0.2 mm diameter; exserted; color nearest RHS 18B.

*Stigma*.—Bifid; about 1.5 mm long and 0.2 mm diameter; color nearest RHS 18B.

Disk florets: About twenty per capitulum; tubular; glabrous; consisting of tepals, staminal tube and pistil; size about 3.5 mm long by 1.0 mm wide at apex;

*Tepals*.—Five; 2.5 mm long and 0.7 mm wide, fused in the basal 2.0 mm, acute apex.

*Tepal color*.—Nearest RHS 8D.

*Staminal tube*.13 Made up of five adnate stamens; about 2.0 mm long.

*Filaments*.—Cylindrical; about 0.7 mm long and 0.1 mm diameter; color nearest RHS NN155A.

*Anther*.—About 1.0 mm long and 0.5 mm across; color nearest RHS 22A.

*Pollen*.—Fine, round, closest to RHS 22A.

*Style*.—Cylindrical; exserted; about 2.0 mm long and 0.2 mm diameter; color nearest RHS 18B.

*Stigma*.—Bifid; reflexing as it matures; about 1.5 mm long; color nearest RHS 18B.

Seed: Flattened deltoid; acute apex and truncate base; surface glabrous; about 2.0 mm long and 0.7 mm across base;

Seed color: Between RHS 165A and RHS 165B in center and RHS 161D around edges;

*Achillea* 'Sassy Summer Lemon' does best in well-drained soils and is tolerant of winter temperatures as low as −35° C. and summer temperatures as high as 38° C. 'Sassy Summer Lemon' resists lodging from heavy winds and rains, but has not shown any tolerance or resistance to diseases common among Yarrow include *botrytis* (*Botrytis cinerea*) and stem rot (*Pythium* and *Phytophthora*) or to insect pests.

I claim:

1. The new and distinct cultivar of *Achillea* plant named 'Sassy Summer Lemon' as described and illustrated.

* * * * *